US00PP34113P2

(12) United States Plant Patent
Lommerse et al.

(10) Patent No.: US PP34,113 P2
(45) Date of Patent: Apr. 5, 2022

(54) ***SALVIA* PLANT NAMED 'PINK SERENADE'**

(50) Latin Name: *Salvia sylvestris*
Varietal Denomination: Pink Serenade

(71) Applicant: FUTURE PLANTS LICENTIE B.V., Lisserbroek (NL)

(72) Inventors: Gerardus Adrianus Petronella Lommerse, Noordwijkerhout (NL); Hendrikus Petrus Lommerse, Lisse (NL)

(73) Assignee: FUTURE PLANTS LICENTIE B.V., Lisserbroek (NL)

( * ) Notice: Subject to any disclaimer, the term of this patent is extended or adjusted under 35 U.S.C. 154(b) by 0 days.

(21) Appl. No.: 17/377,120

(22) Filed: Jul. 15, 2021

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Salvia* plant named 'Pink Serenade', characterized by its upright plant habit; strong and vigorous growth habit; freely flowering habit; long racemes with light purple-colored flowers; and good garden performance.

2 Drawing Sheets

Figure 1:
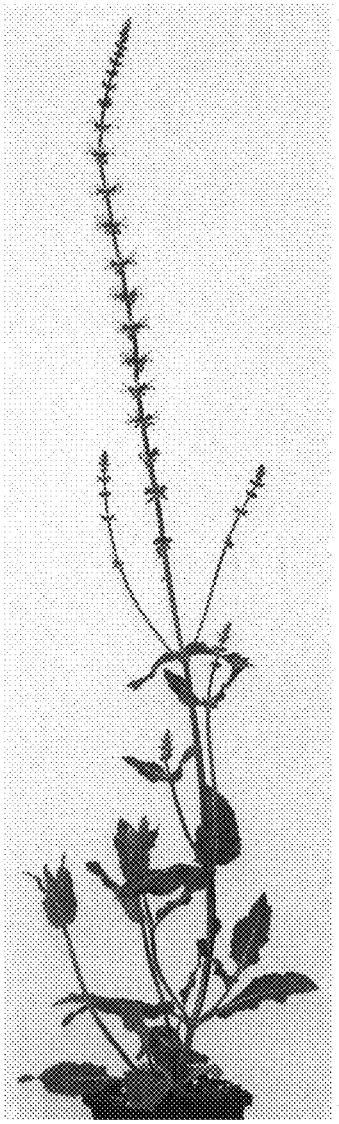

Botanical designation: *Salvia sylvestris*.
Cultivar denomination: 'PINK SERENADE'.

BACKGROUND OF THE INVENTION

The present invention relates to a new and distinct cultivar of *Salvia* plant, botanically known as *Salvia sylvestris* and hereinafter referred to by the name 'Pink Serenade'.

The new *Salvia* plant is a naturally-occurring branch mutation of *Salvia sylvestris* 'Serenade', not patented. The new *Salvia* plant was discovered and selected by the Inventor on a single flowering plant from within a population of plants of 'Serenade' in a controlled environment in Lisserbroek, The Netherlands in June, 2019.

Asexual reproduction of the new *Salvia* plant by softwood cuttings in Lisserbroek, The Netherlands, since June, 2019 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'Pink Serenade'. These characteristics in combination distinguish 'Pink Serenade' as a new and distinct cultivar of *Salvia:*

1. Upright plant habit.
2. Strong and vigorous growth habit.
3. Freely flowering habit.
4. Long racemes with light purple-colored flowers.
5. Good garden performance.

Plants of the new *Salvia* can be compared to plants of the mutation parent, 'Serenade'. Plants of the new *Salvia* differ primarily from plants of 'Serenade' in flower color as plants of the new *Salvia* have light purple-colored flowers whereas plants of 'Serenade' have mauve lilac-colored flowers.

Plants of the new *Salvia* can be compared to plants of 'Pink Delight', disclosed in U.S. Plant Pat. No. 14,965. In side-by-side comparisons, plants of the new *Salvia* differ from plants of 'Pink Delight' in the following characteristics:

1. Plants of the new *Salvia* are taller than plants of 'Pink Delight'.
2. Plants of the new *Salvia* have longer inflorescences with more flowers than plants of 'Pink Delight'.

Plants of the new *Salvia* can also be compared to plants of 'Moulin Rouge', disclosed in U.S. Plant Pat. No. 32,387. In side-by-side comparisons, plants of the new *Salvia* differ from plants of 'Moulin Rouge' in the following characteristics:

1. Plants of the new *Salvia* are taller than plants of 'Moulin Rouge'.
2. Plants of the new *Salvia* have longer inflorescences with more flowers than plants of 'Moulin Rouge'.
3. Flowers of plants of the new *Salvia* are lighter purple in color than flowers of plants of 'Moulin Rouge'.

BRIEF DESCRIPTION OF THE PHOTOGRAPHS

The accompanying colored photographs illustrate the overall appearance of the new *Salvia* plant, showing the colors as true as it is reasonably possible to obtain in colored reproductions of this type. Colors in the photographs may differ slightly from the color values cited in the detailed botanical description which accurately describe the actual colors of the new *Salvia* plant.

The photograph on the first sheet (FIG. 1) comprises a side perspective view of a typical flowering plant of 'Pink Serenade' grown in a container.

Figure 2:
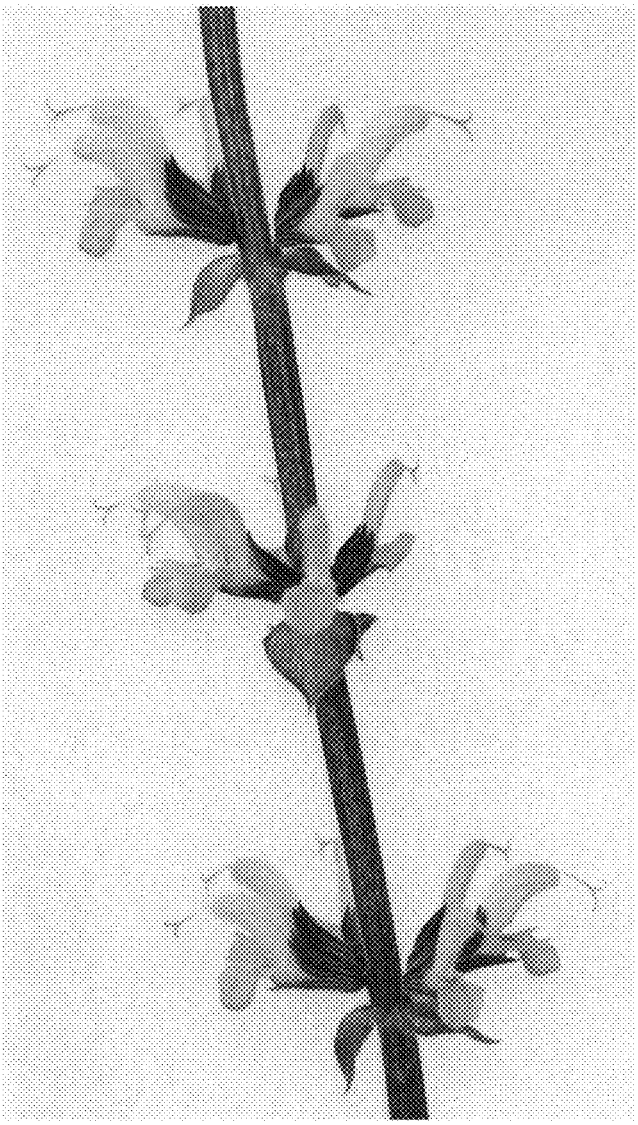

The photograph on the second sheet (FIG. 2) is a close-up view of a typical inflorescence of 'Pink Serenade'.

DETAILED BOTANICAL DESCRIPTION

Plants used for the aforementioned photographs and following description were grown under conditions which closely approximate commercial *Salvia* production conditions in June in 9-cm containers in an outdoor nursery in Lisserbroek, The Netherlands. During the production of the plants, day temperatures ranged from 12° C. to 25° C. and night temperatures ranged from 4° C. to 12° C. Plants were two months from planting when the photographs and description were taken. In the following description, color references are made to The Royal Horticultural Society Colour Chart, 2015 Edition, except where general terms of ordinary dictionary significance are used.

Botanical classification: *Salvia sylvestris* 'Pink Serenade'.

Parentage: Naturally-occurring branch mutation of *Salvia sylvestris* 'Serenade', not patented.

Propagation:

*Type*.—By softwood cuttings.

*Time to initiate roots, summer*.—About 20 days at temperatures about 24° C.

*Time to produce a rooted young plant, summer*.—About six weeks at temperatures about 24° C.

*Root description*.—Medium in thickness, slightly fibrous; typically greyed white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright plant habit; overall plant shape is narrowly ovate to obovate; vigorous growth habit and moderate growth rate.

*Branching habit*.—Freely branching habit with about three primary lateral branches each with about four secondary lateral branches developing per plant; pinching is not required, but will improve branching and flowering potential.

*Plant height, soil level to top of foliar plane*.—About 32.1 cm.

*Plant height, soil level to top of floral plane*.—About 81.4 cm.

*Plant width*.—About 21.6 cm.

*Primary branch description*.—Length (excluding inflorescence): About 31.6 cm. Diameter: About 4 mm. Internode length: About 11.7 cm. Shape: Quadrangular. Strength: Strong. Branch angle: About 15° to 70° from vertical. Texture and luster: Moderately pubescent; slightly glossy. Color, developing: A blend of close to N186C and 200B strongly tinged with close to 145A. Color, developed: A blend of close to N186C and 200A strongly tinged with close to 144A; at the internodes, close to 148A tinged with close to 184A.

Leaf description:

*Arrangement*.—Opposite; simple.

*Length*.—About 8.7 cm.

*Width*.—About 4.1 cm.

*Shape*.—Narrowly ovate.

*Apex*.—Acute.

*Base*.—Truncate.

*Margin*.—Crenate to dentate.

*Texture and luster, upper surface*.—Mostly glabrous with pubescence along midvein; moderately rugose; moderately glossy.

*Texture and luster, lower surface*.—Pubescent; moderately rugose; slightly glossy.

*Venation pattern*.—Pinnate; veins furrowed.

*Color*.—Developing leaves, upper surface: Close to 143A. Developing leaves, lower surface: Close to 138A. Fully expanded leaves, upper surface: Close to NN137A; venation, close to 193A to 193B. Fully expanded leaves, lower surface: Close to 147B; venation, close to 146D.

*Petioles*.—Length: About 1.1 cm. Diameter: About 2.5 mm by 4 mm. Strength: Strong. Texture and luster, upper and lower surfaces: Sparsely pubescent; slightly glossy. Color, upper surface: Close to 182C; at the margins, close to 143B. Color, lower surface: Close to 146D; at the margins, close to 143B.

Flower description:

*Flower arrangement and shape*.—Single bilabiate flowers arranged on long terminal verticillasters; flowers face mostly outwardly.

*Flowering habit*.—Freely flowering habit, about 168 flowers per inflorescence.

*Natural flowering season*.—Continuous flowering from the late spring into the autumn in The Netherlands; plants begin flowering about four weeks after planting.

*Flower longevity on the plant*.—About ten days; flowers not persistent.

*Fragrance*.—Not detected; leaves, however, are aromatic.

*Flower buds*.—Length: About 6 mm. Diameter: About 2 mm. Shape: Obovate. Texture and luster: Moderately pubescent; matte. Color: Sepals, close to 63A; petals, a blend of close to N186C and 200A, proximally, close to 146D.

*Inflorescence length, from lowest whorl of flowers to apex*.—About 43.6 cm.

*Inflorescence diameter*.—About 3.3 cm.

*Flower height*.—About 1 cm.

*Flower diameter*.—About 4.5 mm.

*Flower length (depth)*.—About 1.5 cm.

*Flower throat diameter*.—About 1 mm.

*Flower tube length*.—About 6 mm.

*Flower tube diameter*.—About 1.75 mm by 2.5 mm.

*Petals*.—Arrangement: Five petals with two upper petals fused forming a galea and three lower petals fused forming a broader lower protruding lip. Upper galea length: About 6 mm. Upper galea width: About 1 mm. Lower lip length: About 5 mm. Lower lip width: About 4.5 mm. Shape: Upper galea, obovate, folded; lower lip, center lobe, broadly obovate and lateral lobes, narrowly obovate. Upper galea apex: Emarginate. Lower lip apex: Center lobe, shallowly emarginate and lateral lobes, obtuse. Base: Fused. Margin: Entire; upper galea, not undulate and lower lip, moderately undulate with center lobe, concave. Texture and luster, upper surface: Smooth, glabrous;

slightly velvety; matte. Texture and luster, lower surface: Densely pubescent; slightly velvety; matte. Texture and luster, throat: Smooth, glabrous; matte. Texture and luster, tube: Smooth, glabrous; matte. Color: Galea, when opening, upper and lower surfaces: Close to 73C. Galea, fully opened, upper and lower surfaces: Close to 75B; venation, close to 75B; color does not change with subsequent development. Lower lip, when opening, upper surface: Close to N74D. Lower lip, when opening, lower surface: Close to 75B. Lower lip, fully opened, upper surface: Close to N75C; venation, close to N75C; color does not change with subsequent development. Lower lip, fully opened, lower surface: Close to N75C to N75D; venation, close to N75C to N75D; color does not change with subsequent development. Throat: Close to N75D; venation, close to N75D. Tube: Close to N155A; venation, close to N155A.

*Calyx*.—Arrangement: Two fused sepals to form a campanulate calyx; lower 70% of calyx is fused. Calyx length: About 7 mm. Calyx diameter: About 3 mm by 5 mm. Sepal length: About 7 mm. Sepal width: About 3 mm. Sepal shape: Oblanceolate. Sepal apex: Upper sepal, emarginate and lower sepal, cleft. Sepal margin: Entire. Sepal texture and luster, inner surface: Smooth, glabrous; matte. Texture and luster, outer surface: Moderately pubescent; matte. Color: When developing and fully developed, inner surface: Close to 146D; venation, close to 147A. When developing, outer surface: A blend of close to N186C and 200A; proximally, close to 146D. Fully developed, outer surface: Close to 147B; venation, close to 147A; distally, a blend of close to N186C and 200A.

*Peduncles*.—Length: About 51.4 cm. Diameter: About 3 mm. Strength: Strong. Aspect: Primary peduncles, erect; lateral peduncles, about 30° from peduncle axis. Texture and luster: Moderately pubescent; matte; quadrangular and longitudinally ridged. Color: A blend of close to N186C and 200A tinged with close to 144C; at longitudinal ridges, close to N186C.

*Pedicels*.—Length: About 2.5 mm. Diameter: About 0.5 mm. Strength: Moderately strong. Aspect: About 60° from peduncle axis. Texture and luster: Densely pubescent; matte. Color: Close to N200B.

*Reproductive organs*.—Stamens: Quantity per flower: Two. Filament length: About 2 mm. Filament color: Close to 75D. Anther size: About 0.3 mm by 0.75 mm. Anther shape: Narrowly oblong. Anther color: Close to 200A. Pollen amount: None observed. Pistils: Quantity per flower: One. Pistil length: About 1.5 cm. Stigma diameter: About 2 mm. Stigma shape: Cleft. Stigma color: Close to 77B. Style length: About 1.4 cm. Style color: Close to 77B; proximally, close to 155A. Ovary color: Close to 16A.

*Flower bracts*.—Quantity and arrangement: Two, opposite, at base of pedicels. Length: About 1 cm. Width: About 8 mm. Shape: Broadly cordate. Apex: Cuspidate. Base: Broadly truncate. Margin: Entire; pubescent. Texture and luster, upper surface: Moderately pubescent; matte. Texture and luster, lower surface: Glabrous; matte. Color, upper surface: Darker than 148A; venation, close to 143A. Color, lower surface: Close to 147A to 147B; venation, close to 143A.

*Seeds and fruits*.—To date, seed and fruit production has not been observed.

Pathogen & pest resistance: To date, plants of the new *Salvia* have not been noted to be resistant to pathogens and pests common to *Salvia*.

Garden performance: Plants of the new *Salvia* have exhibited good tolerance to rain, wind and temperatures ranging from −23° C. to 40° C. and to be suitable for USDA Hardiness Zones 5 to 10.

It is claimed:

1. A new and distinct *Salvia* plant named 'Pink Serenade' as illustrated and described.

* * * * *